United States Patent [19]

Southgate et al.

[11] 4,395,122

[45] Jul. 26, 1983

[54] DEFECT DETECTION SYSTEM

[75] Inventors: Peter D. Southgate; Istvan Gorog, both of Princeton, N.J.

[73] Assignee: RCA Corporation, New York, N.Y.

[21] Appl. No.: 258,759

[22] Filed: Apr. 29, 1981

[51] Int. Cl.³ ............................................. G01N 21/89
[52] U.S. Cl. ...................................... 356/237; 250/562
[58] Field of Search ................... 356/237, 445–448; 250/562, 563, 572

[56] References Cited

U.S. PATENT DOCUMENTS

| | | | |
|---|---|---|---|
| 3,842,194 | 10/1974 | Clemens | 178/6.6 A |
| 4,030,835 | 6/1977 | Firester et al. | 356/111 |
| 4,044,379 | 8/1977 | Halter | 358/128 |
| 4,069,484 | 1/1978 | Firester et al. | 346/33 |
| 4,092,068 | 5/1978 | Lucas et al. | 356/73 |
| 4,155,098 | 5/1979 | Roach et al. | 356/237 |
| 4,180,830 | 12/1979 | Roach | 356/237 |
| 4,197,011 | 4/1980 | Hudson | 356/354 |
| 4,352,564 | 10/1982 | Roach | 356/237 |
| 4,363,118 | 12/1982 | Roach et al. | 356/237 |

*Primary Examiner*—Bruce Y. Arnold
*Attorney, Agent, or Firm*—E. M. Whitacre; J. S. Tripoli; J. E. Roehling

[57] ABSTRACT

A flaw detection system optically detects defects on the surface of a grooved video disc surface. A beam of light incident on the surface being inspected is reflected thereby into a series of diffraction order cones. A cylindrical lens converges the higher diffraction order cones onto a split photodetector. When the light beam which scans the disc surface passes over a surface defect, such as a hillock, the reflected beam is deflected first to one photosensitive surface of the split photodetector and then to the other, thus providing an output from the photodetector to indicate the presence of such a defect.

10 Claims, 4 Drawing Figures

DISC MOTION

DEFECT DETECTION SYSTEM

The present invention relates generally to novel systems employing optical techniques for detecting defects in a flat surface and, more particularly, to optical defect detection systems which may be employed for detecting defects on a surface of a spirally grooved information record, such as a video disc, of a type described in U.S. Pat. No. 3,842,194 to J. K. Clemens.

The Clemens Patent discloses a video disc for use with a playback system of the variable capacitance type. In one configuration of the Clemens' system, information representative of recorded picture and sound is encoded in the form of a relief pattern in a relatively fine spiral groove on the surface of a disc record. For example, groove widths of approximately 2.6 micrometers and groove depths of about 0.5 micrometers may be used. During playback, capacitive variations between a conductive electrode on a stylus and a conductive property of the disc record are sensed to recover the prerecorded information.

In accordance with the Clemens' format, the video information may be recorded as relatively short (e.g. 0.6–1.6 micrometers) relief variations along the length of the spiral groove. Illustratively, the method of recording may be of a type shown in U.S. Pat. No. 4,044,379 to J. B. Halter. Pursuant to the Halter method, an electromechanically-driven stylus (e.g., of diamond) having a triangular shape, responsive to a combined video and audio signal, records relatively short geometric variations, representative of the time variations of the signal, on a surface of a metal substrate. After the electromechanical recording operation, the recorded surface of the metal substrate has a relief pattern corresponding to that which is desired in the final record. In the replicating process, masters are made from the substrate. Molds are then made from the masters and stampers are made from the molds. The stampers are used in the process of pressing a vinyl record having the desired relief pattern.

During each of the above-identified record manufacturing processes, small irregularities (e.g., protuberances or hillocks) may appear in the surface of the grooved part. These irregularities may interfere during the playback of a vinyl record with a stylus or other mechanical pick-up device. Various kinds of flaws, such as small protuberances or hillocks, are difficult to detect by direct microscopic examination.

In U.S. Pat. No. 4,092,068 issued on May 30, 1978 to J. M. Lucas, et al. entitled "Surface Sensor", a system is described for detecting surface characteristics (e.g., roughness and dirt) of a paper web. In the Lucas system a beam of light is directed at a near normal angle to impinge on the surface to be inspected and a pair of detectors are arranged above the incident surface to collect scattered light reflected therefrom. If the area of the surface to be illuminated is not perpendicular to the incident beam (indicative of a peak or valley) the amount of light reflected to and sensed by the detectors will not be equal and the imbalance will be indicative of the slope of the surface at the point of incidence.

This system may work well for a surface such as paper which has a fairly uniform wide-angle scattering characteristic, however, it is not well suited for inspecting grooved, mirror-like, black surfaces such as a video disc described in the Clemens patent. The grooved surface of a Clemens disc acts as a diffraction grating which diffracts the majority of the light out of the specular direction and into higher diffraction orders. For example, in a triangular-shaped grooved structure having approximately 10,000 grooves per inch the majority of the light reflected off of the disc surface can be diffracted into the second and third diffraction orders. The black surface of the replica discs further reduces the amount of light reflected off of the surface being inspected—only a few percent of the incident light is reflected.

In accordance with the principles of the present invention, a flaw detection system is provided for detecting bump-type defects on grooved, specular, black surfaces which are difficult to detect by direct microscopic examination and prior art optical schemes.

Further, in accordance with the principles of the present invention, a flaw detection system for detecting protuberances on a surface of a disc having a groove formed thereon is provided. The system comprises a source of illumination for providing a beam of light and means for focusing the beam of light to a spot on the disc surface. A means for detecting the light beam reflected from the surface has first and second light sensitive surfaces. The detecting means is positioned such that the first light sensitive surface is illuminated, to the relative exclusion of the second light sensitive surface, by the light beam when it is reflected from a first portion of a protuberance on the disc surface, the second light sensitive surface is illuminated, to the relative exclusion of the first light sensitive surface, by the light beam when it is reflected from a second portion of the protuberance and the first and second light sensitive surfaces are illuminated substantially equally by the light beam when it is reflected from a portion of the disc surface where protuberances are absent. Also, the system comprises means, responsive to the detecting means, for indicating the presence of a protuberance.

In accordance with one aspect of the invention, the flaw detection system further includes an anamorphic optical system, such as a cylindrical lens or plurality of lenses which produce unequal magnification along two perpendicular axes in an image plane. The groove structure in the region of the spot illuminated by the light beam serves as a diffraction grating for diffracting light reflected from the illuminated spot to form a zero diffraction order cone and higher diffraction order cones of light. The anamorphic system focuses one or more of the diffraction order cones onto the first and second light sensitive surfaces of the detecting means. The zero order cone may also be focused onto the light sensitive surfaces.

Other features and advantages of the invention will be more fully understood from the following detailed description of the preferred embodiment, the appended claims and the accompanying drawing in which:

Figure 1:
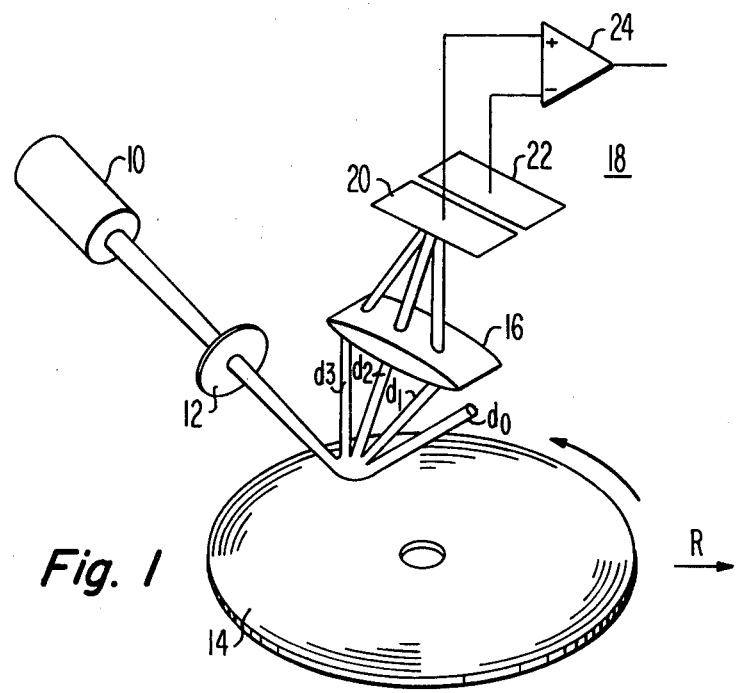
FIG. 1 shows, in a perspective view, a grooved disc defect detection system embodying the principles of the present invention.

Referring to FIG. 1, a coherent light beam from a light source 10 (illustratively, in the form of a He-Ne laser) is focused by lens 12 to a spot on the surface of disc 14. Illustratively, the light beam is focused to a spot of about 0.025 mm in diameter. The light beam converges to the spot at the surface of disc 14, forming a light spot of such a size that a plurality of convolutions of the disc's spiral groove (e.g., 10 convolutions of a 10,000 convolutions per inch disc record) are illuminated.

The groove structure in the illuminated region on the surface of the disc provides a regular pattern of depressions and elevations which effectively serves as a diffraction grating (having a grating pitch determined by the groove convolution pitch) for diffracting the light reflected from the disc surface. This light diffraction results in the formation of an undeviated zero diffraction order cone of light $d_0$ and a plurality of additional deviated cones, $d_1$, $d_2$, $d_3$, of light corresponding to higher diffraction orders.

The orientation of the incident beam is desirably such that the axis of the incident beam lies in a nonparallel and at a chosen angle (e.g. 30°) with respect to the central axis of disc 14 and is desirably positioned in a plane which contains the central axis. Rotating disc 14 is translated in a radial direction R (by means not shown in the figures) causing the illuminating light spot to scan the disc surface in a coarse spiral pattern, having a pitch appreciably greater than the pitch of the spiral groove (illustratively, the laser spot scans a spiral of about 0.025 mm pitch).

A plurality of the diffraction order cones $d_1$, $d_2$, $d_3$ are collected by cylindrical lens 16 and focused in one plane onto split optical detector 18 having photosensitive regions 20, 22. Illustratively, optical detector 18 may be a split photodetector such as a PIN-Spot/9D manufactured by United Detector Technology, Inc. of Santa Monica, Calif. Photosensitive region 20 is coupled to one input terminal of differential amplifier 24 and region 22 to the other input terminal of amplifier 24.

Figure 2A:
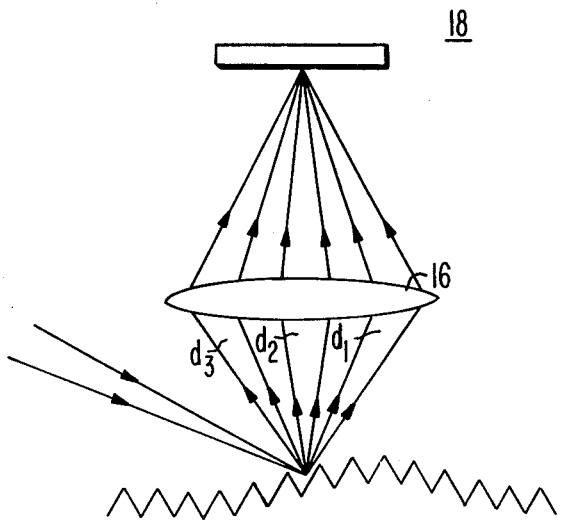
FIGS. 2a and 2b show a portion of the defect detection system of FIG. 1 relating to the processing of the reflected diffraction orders.
Figure 2B:
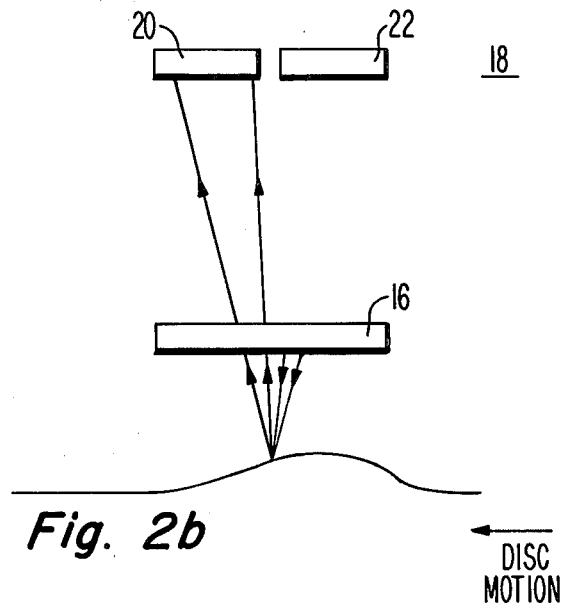

An explanation of the operation of the flaw detection system will now be made with reference to FIGS. 2a and 2b where FIG. 2a shows the optical system as viewed along a cut taken radially through the disc and FIG. 2b shows the optical system as viewed tangentially. The light diffracted from the disc forms a fan of diffracted beams $d_1$, $d_2$, $d_3$. The fan is collected by cylindrical lens 16 and focused thereby on split optical detector 18. When a bump (or a hollow) on the disc surface passes by the light spot as the disc rotates, the image of the spot on the split detector will move from one photosensitive region (e.g., detector half 20) to the other (e.g., detector half 22). Thus, the output from differential amplifier 24 (FIG. 1) will change to indicate detection of a bump. In this arrangement, the system is aligned such that the spot image initially (i.e., on flat portions of the disc surface) falls equally on each half of the detector. The function of the cylindrical lens is to reconverge the beam spread corresponding to groove diffraction to a small region on the detector surface while simultaneously permitting beam deflection orthogonal to the plane of diffraction which is indicative of a bump to appear at the detector.

One advantage of the present balanced detector scheme is its insensitivity to certain surface formations. For example, if the disc has a dark or bright spot on it, the intensity of the light received by each half of the detector will change equally, thus the output of the differential amplifier will not change. Similarly, the output is insensitive to dust particles which uniformly scatter the light.

Bumps or hillocks on the disc surface which are of significance may have slopes which are small, considerably less than one degree. In this case, the beam deflection due to disc warpage may exceed the deflection due to bumps and, therefore, upset the balance between detector halves. To reduce the effect of disc warpage, the flaw detection system may be provided with a servo control arrangement for maintaining, on the average, the image of the spot centered on the detector.

Figure 3:
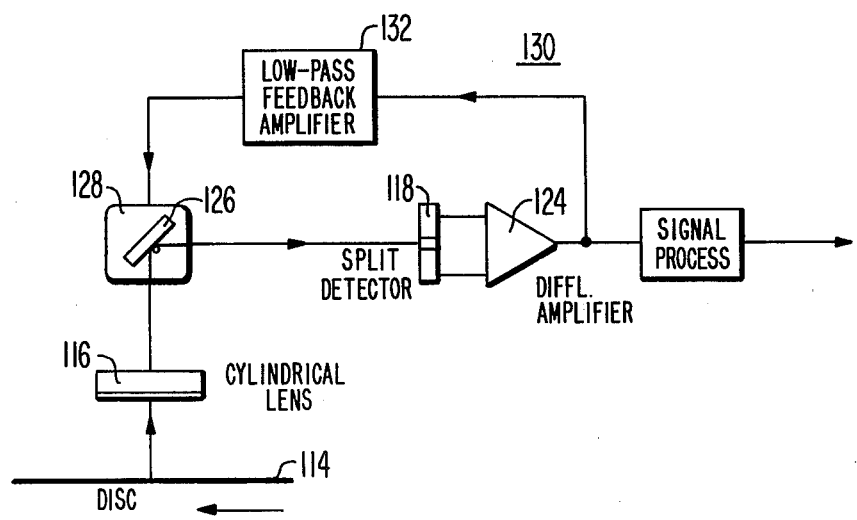
FIG. 3 shows, partially in block diagram form, a defect detection system having a feedback network constructed in accordance with the principles of the present invention.

Referring to FIG. 3, part of the light fan is intercepted by a mirror 126 actuated by a galvanometer 128 and reflected toward the split photodetector 118. The light reflected from the disc 114 passes through cylindrical lens 116 which focuses it, in a horizontal plane onto the split photodetector 118. The signal from the detector is then amplified in differential amplifier 124 which provides an output proportional to the difference of the responses of the two halves of the photodetector. A feedback servo system 130 is provided to deflect the galvanometer controlled mirror for maintaining, on the average, the image of the spot centered on detector 118. The time constant of feedback amplifier 132 is chosen such that disc warpage of wide spatial extent are followed while small diameter hillocks or hollows on the disc surface are not.

The defect detection principles of the present invention are applicable to optical inspection of a video disc surface having closely and uniformly spaced spiral groove convolutions at various stages of the record mastering and replicating processes. However, it will be appreciated by those of skill in the art that the defect detection principles of the present invention may be used for optical inspection of other flat surfaces.

What is claimed is:

1. A flaw detection system for detecting protuberances on a surface of a disc having a groove formed thereon, said system comprising:

a source of illumination for providing a beam of light;

means for focusing said beam of light to a spot on the surface of said disc;

means for detecting the light beam reflected from said surface, said detecting means having first and second light sensitive surfaces, said detecting means being positioned such that said first light sensitive surface is illuminated, to the relative exclusion of said second light sensitive surface, by said light beam when said light beam is reflected from a first portion of a protuberance on said disc surface, said second light sensitive surface is illuminated, to the relative exclusion of said first light sensitive surface, by said light beam when said light beam is reflected from a second portion of said protuberance and said first and said second light sensitive surfaces are illuminated substantially equally by said light beam when said light beam is reflected from a portion of said disc surface where protuberances are absent;

the structure of the groove in the region of the spot illuminated by the light beam serving as a diffraction grating for diffracting light reflected from said illuminated spot to form a zero diffraction order cone and higher diffraction order cones of light;

an anamorphic optical system for focusing a plurality of said higher diffraction order cones onto said first and second light sensitive surfaces; and means, responsive to said detecting means, for indicating the presence of said protuberance.

2. The system according to claim 1 wherein said anamorphic optical system comprises a cylindrical lens.

3. The system according to claim 2 wherein said detecting means comprises a split photodetector wherein said first light sensitive surface represents a first half of the detector surface of said split photodetector and wherein said second light sensitive surface represents a second half of the detector surface of said split photodetector.

4. The system according to claim 3 wherein said indicating means includes a differential amplifier having a first differential input connected to a first output of said split photodetector and having a second differential input connected to a second output of said split photodetector, the output signal of said differential amplifier being a function of the difference in light intensity on said first and second light sensitive surfaces.

5. The system according to claim 4 further comprising means for establishing relative motion between said beam of light and said disc surface.

6. A flaw detection system for detecting protuberances on a surface of a disc having a spiral groove formed thereon, said system comprising:
a source of illumination for providing a beam of light;
means for focusing said beam of light to a spot on the surface of said disc;
means for establishing relative motion between said beam of light and said disc surface;
means for detecting the light beam reflected from said surface, said detecting means having first and second light sensitive surfaces, said detecting means being positioned such that said first light sensitive surface is illuminated, to the relative exclusion of said second light sensitive surface, by said light beam when said light beam is reflected from a first portion of a protuberance on said disc surface, said second light sensitive surface is illuminated, to the relative exclusion of said first light sensitive surface, by said light beam when said light beam is reflected from a second portion of said protuberance and said first and second light sensitive surfaces are illuminated substantially equally by said light beam when said light beam is reflected from a portion of said disc surface where protuberances are absent;
the structure of the groove convolutions in the region of the spot illuminated by the light beam serving as a diffraction grating for diffracting light reflected from the illuminated spot to form a zero diffraction order cone and higher diffraction order cones of light;
an anamorphic optical system for focusing a plurality of said higher diffraction order cones onto said first and second light sensitive surfaces;
a mirror, interposed between said disc surface and said detecting means, for deflecting the light beam reflected from said disc surface to maintain, on the average, the light reflected from said surface centered on said detecting means;
means, coupled to said mirror, for providing motion to said mirror;
means, responsive to said detecting means, for indicating the presence of said protuberance.

7. The system according to claim 6 further comprising a feedback arrangement coupling the output signal of the indicating means to the motion providing means for minimizing the effect of disc warpage on the output signal of the system.

8. The system according to claim 7 wherein said anamorphic optical system comprises a cylindrical lens.

9. The system according to claim 8 wherein said indicating means includes a differential amplifier having a first differential input connected to a first output of said split photodetector and having a second differential input connected to a second output of said split photodetector, the output signal of said differential amplifier being a function of the difference in light intensity on said first and second light sensitive surfaces.

10. The system according to claim 9 wherein said detecting means comprises a split photodetector wherein said first light sensitive surface represents a first half of the detector surface of said split photodetector and wherein said second light sensitive surface represents a second half of the detector surface of said split photodetector.

* * * * *